United States Patent
Nawrocki et al.

(10) Patent No.: US 7,041,088 B2
(45) Date of Patent: May 9, 2006

(54) MEDICAL DEVICES HAVING DURABLE AND LUBRICIOUS POLYMERIC COATING

(75) Inventors: Jesse G. Nawrocki, Annandale, NJ (US); Dennis D. Jamiolkowski, Long Valley, NJ (US)

(73) Assignee: Ethicon, Inc., Somerville, NJ (US)

( * ) Notice: Subject to any disclaimer, the term of this patent is extended or adjusted under 35 U.S.C. 154(b) by 231 days.

(21) Appl. No.: 10/678,560

(22) Filed: Oct. 3, 2003

(65) Prior Publication Data

US 2004/0071988 A1 Apr. 15, 2004

Related U.S. Application Data

(60) Provisional application No. 60/418,054, filed on Oct. 11, 2002.

(51) Int. Cl.
C08L 83/00 (2006.01)
B32B 9/04 (2006.01)
A61M 25/00 (2006.01)

(52) U.S. Cl. .......... 604/265; 428/447; 428/500; 525/100; 525/446

(58) Field of Classification Search .......... 604/265; 525/100–106, 446, 474; 428/447, 500, 523
See application file for complete search history.

(56) References Cited

U.S. PATENT DOCUMENTS

| | | | |
|---|---|---|---|
| 3,434,869 A | | 3/1969 | Davidson |
| 3,585,674 A | | 6/1971 | Gajewski et al. |
| 4,844,986 A | | 7/1989 | Karakelle et al. |
| 5,001,009 A | | 3/1991 | Whitbourne |
| 5,026,607 A | | 6/1991 | Kiezulas |
| 5,266,359 A | | 11/1993 | Spielvogel |
| 5,331,027 A | | 7/1994 | Whitbourne |
| 5,477,756 A | | 12/1995 | Trankiem et al. |
| 5,536,582 A | | 7/1996 | Prasad et al. |
| 5,578,075 A | | 11/1996 | Dayton |
| 5,773,563 A | | 6/1998 | Shalaby |
| 5,911,711 A | | 6/1999 | Pelkey |
| 5,968,091 A | | 10/1999 | Pinchuk et al. |
| 5,997,517 A | | 12/1999 | Whitbourne |
| 6,015,398 A | | 1/2000 | Arimatsu et al. |
| 6,071,266 A | * | 6/2000 | Kelley .......... 604/265 |
| 6,110,483 A | | 8/2000 | Whitbourne et al. |
| 6,156,824 A | | 12/2000 | Yamada et al. |
| 6,176,849 B1 | | 1/2001 | Yang et al. |
| 6,179,817 B1 | | 1/2001 | Zhong |
| 6,189,536 B1 | | 2/2001 | Martinez et al. |
| 6,306,176 B1 | | 10/2001 | Whitbourne |
| 6,331,186 B1 | | 12/2001 | Wang |
| 6,358,556 B1 | | 3/2002 | Ding et al. |
| 6,361,819 B1 | | 3/2002 | Tedeschi et al. |
| 6,368,658 B1 | | 4/2002 | Schwarz et al. |
| 6,395,325 B1 | | 5/2002 | Hedge et al. |
| 6,416,613 B1 | | 7/2002 | Patrick et al. |
| 6,458,867 B1 | | 10/2002 | Wang et al. |
| 6,558,409 B1 | | 5/2003 | Roby |
| 6,841,255 B1 | * | 1/2005 | Deppisch et al. ........ 428/425.5 |
| 2001/0003796 A1 | | 6/2001 | Yang et al. |
| 2001/0021832 A1 | | 9/2001 | Numao et al. |
| 2001/0027299 A1 | | 10/2001 | Yang et al. |
| 2002/0016574 A1 | | 2/2002 | Wang et al. |
| 2002/0068180 A1 | | 6/2002 | Yang et al. |
| 2003/0114882 A1 | | 6/2003 | Roby et al. |

FOREIGN PATENT DOCUMENTS

| | | |
|---|---|---|
| EP | 0407965 A1 | 1/1991 |
| EP | 0 302 625 B2 | 1/1997 |
| EP | 0-627 474 B1 | 10/2000 |

OTHER PUBLICATIONS

Product data sheet for Dow Corning MB50-002.*
E-mail from a Dow Corning employee concerning Dow Corning MB50-002.*
Tim A. Fischell, MD, Polymer Coatings for Stents; Circulation, 1996; 94: 1494–1495.
Attar S. Chawla et al; Characterization of Plasma Polymerized Silicone Coatings Useful as Biomaterials; Journal of Biomedical Materials Research, vol. 18, 537–545 (1984).
Elliot L. Chaikof, MD et al.; Development and Evaluation of a New Polymeric Material for Small Caliber Vascular Prostheses; Journal of Surgical Research 47, 193–199 (1989).
Search Report EP 03 25 6398, mailed Jan. 23, 2004 which relates to U.S. Appl. No. 10/678,560, filed Oct. 3, 2003.

* cited by examiner

*Primary Examiner*—Randy Gulakowski
*Assistant Examiner*—Marc S. Zimmer

(57) ABSTRACT

A medical device having a contact surface exposed repeatedly to bodily tissue is disclosed. The contact surface is coated with a silicone polymer and one or more non-silicone hydrophobic polymers. The preferred medical device is a surgical needle, and the preferred coating is a polydimethylsiloxane and polypropylene wax hydrocarbon mixture. The incorporation of the non-silicone hydrophobic polymer increases the durability of the coating on the device without sacrificing lubricity.

13 Claims, 2 Drawing Sheets

MEDICAL DEVICES HAVING DURABLE AND LUBRICIOUS POLYMERIC COATING

This application claims the benefit of provisional application Ser. No. 60/418,054, filed on Oct. 11, 2002.

BACKGROUND OF THE INVENTION

This invention relates to coated medical devices. More specifically, it relates to medical devices which have a contact surface exposed repeatedly to bodily tissue, and where the contact surface has a coating to enhance lubricity while providing the durability necessary to provide that lubricity during the repeated exposure to the tissue.

Coated medical devices, which repeatedly come into contact with bodily tissue, for example surgical needles, are required to be lubricious, yet durable to withstand the multiple contacts with tissue. However, lubricity is often sacrificed at the expense of making a more durable coating that adheres well to medical devices. There are many coating materials that are extremely lubricious, but either do not adhere well to the desired substrates or easily wear off the substrate during use. Likewise, many extremely durable coatings exist, but these coatings are not considered lubricious. Consequently, conventional coated medical devices are unable to maintain lubricity as the devices are used successively because the coatings wear away, such as with a surgical needle that is passed through tissue a number of times.

A highly favored lubricious material that is used as a coating for many medical devices such as surgical needles and catheters is silicone. However, as discussed above in the context of conventional lubricious coating materials, the silicone coating generally wears off the medical device with repeated exposure to tissue. For example, when a needle coated with silicone is successively passed through tissue during wound closure, the silicone coating wears off appreciably with each pass, resulting in an increase in penetration force each time the needle is passed through the tissue.

Examples abound in connection with enhancing the properties of silicone coated medical devices by adding ingredients to modify the overall properties of the silicone coating. For example, hydrophilic surfactants, including hydrophilic polymeric surfactants, have been mixed with silicone coating solutions and applied to medical devices such as catheters and needles. Unfortunately, the incorporation of these hydrophilic polymers does not add significantly to the durability of the silicone coating on these medical devices.

In view of the inability to develop a coating for a medical device which provides lubricity without sacrificing the durability of the coating over successive uses, what is needed is a coated medical device, in particular a medical device coated with a silicone, which will provide these properties simultaneously.

SUMMARY OF THE INVENTION

In its broadest embodiment, the invention is a medical device having a contact surface exposed repeatedly to bodily tissue. The contact surface of the medical device is coated with an effective amount of a coating comprising a silicone polymer and a non-silicone hydrophobic polymer.

The coating on the medical device can be a mixture comprising the silicone polymer and the non-silicone hydrophobic polymer. Alternatively, the coating may comprise an inner layer of the non-silicone hydrophobic polymer and an outer layer of the silicone polymer depending on the material properties and rheology of the non-silicone hydrophobic polymer.

Surprisingly, incorporating the non-silicone hydrophobic polymer into the polymeric coating that is coated onto the contact surface of the medical device provides the contact surface with the requisite lubricity, but without sacrificing the durability of the lubricious coating during repeated exposure to bodily tissue. Further, the advantages of incorporating the non-silicone hydrophobic polymer into the coating contrast significantly with conventional silicone coatings, which sometimes incorporate hydrophilic polymers.

The medical device of this invention can be used in any healthcare application where it is desirable to provide a lubricious contact surface exhibiting durability during successive use, for example, a surgical needle that is passed through bodily tissue multiple times. The medical device of this invention may be composed of any desirable material, including metallic, polymeric, ceramic, or any combination of these material types.

DETAILED DESCRIPTION OF THE PREFERRED EMBODIMENTS

Figure 1:
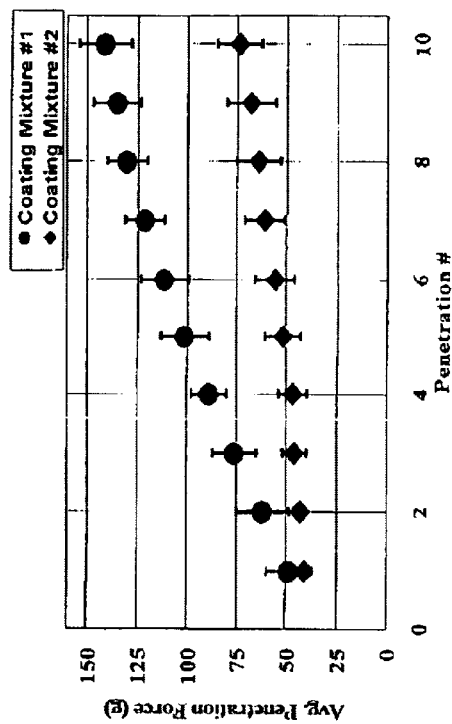
FIG. 1 is a graph illustrating penetration force as a function of number of passes for needles coated with the coating mixtures described in Example 1.
Figure 2:
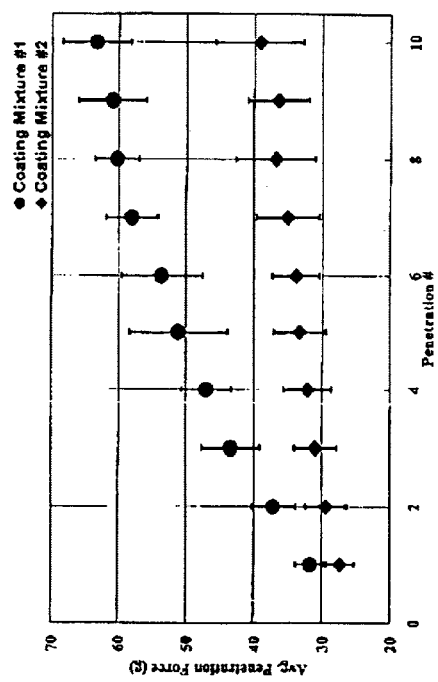
FIG. 2 is a graph illustrating penetration force as a function of number of passes for needles coated with the coating mixtures described in Example 2.
Figure 3:
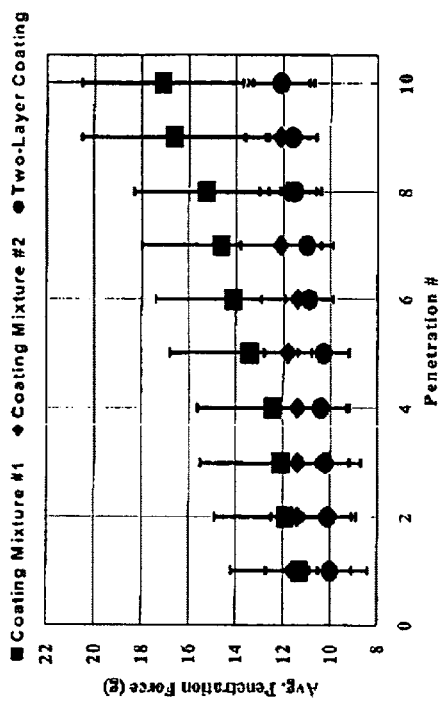
FIG. 3 is a graph illustrating penetration force as a function of number of passes for needles coated with the two layer coating described in Example 3.
Figure 4:
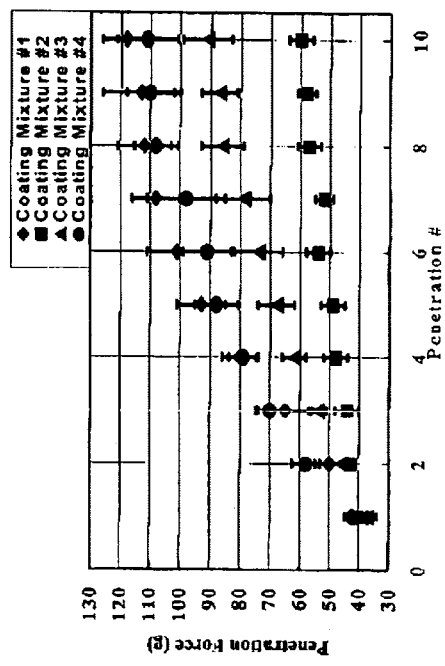
FIG. 4 is a graph illustrating penetration force as a function of number of passes for needles coated with the coating mixtures described in Example 4.

The medical device of this invention can be any device adapted for use in the medical or surgical fields that has a contact surface repeatedly exposed to bodily tissue. Alternatively, a medical device according to this invention can be any device adapted to facilitate the extraction of interstitial fluid, blood or other bodily fluids for the measurement of analytes, including, for example, hollow needles positioned through the surface of the skin for the purpose of continuously or periodically extracting blood or interstitial fluid for the purpose of measuring glucose. Examples of medical devices included within this class are medical devices, which are insertable into or implantable within the body at a targeted site, or otherwise come into contact with tissue on or within the body. Specific examples of medical devices within the scope of this invention include surgical needles, scalpel blades, stents and catheters. The medical devices preferably have a contact surface that is exposed to a sliding or cutting application during use. In a preferred embodiment, the medical device has a contact surface, which includes a penetrating portion, or a sharp surface, where these portions can become "dulled" during repeated use when a conventional lubricious coating, such as a silicone coating, is applied to its surface. Dulled in this application refers to an increase in force or friction with repeated use.

The most preferred medical device that has a contact surface repeatedly exposed to bodily tissue is a surgical needle. The preferred surgical needles are typically made of a metallic alloy, in particular, but not limited to, stainless steels such as 420 stainless steel, 455 stainless steel, Ethalloy stainless steel (U.S. Pat. Nos. 5,000,912 and 5,651,843) and 302 stainless steel. A variety of needle geometries can be used, for example taper points, taper cut, cutting edge needles, bayonet-shaped needles, I-beam, square body, and round body configurations.

The coating for the contact surface of the medical device preferably contains two or more polymer materials. One of the polymers is a silicone. The preferred polymeric silicones are the polysiloxanes, in particular the polyalkylsiloxanes. A preferred polyalkylsiloxane is polydimethylsiloxane. The most preferred silicone polymer is polydimethylsiloxane that is hydroxy-terminated such as MED4162 by NuSil Technology. The silicone polymer may contain small amounts (typically <5 wt %) of other ingredients, which are compatible with the polymer. For example, methyl hydrogen siloxane may be included in the coating. Any minor ingredients are typically catalysts or silicone-containing compounds.

The second polymer for coating on the contact surface of the medical device is a non-silicone hydrophobic polymer. As used herein, a hydrophobic polymer is a polymer that generally lacks an affinity for water, and are readily known and recognized by those skilled in the art (in contrast, for example, to polymeric surfactants, and polyalkylene glycols such as polyethylene glycol, which are hydrophilic in nature). More specifically, we believe that a hydrophobic polymer as it relates to this invention is generally a polymer with a critical surface tension of less than about 50 mN/m. In the preferred embodiment of this invention, the hydrophobic polymer is a thermoplastic polymer. Preferably, the hydrophobic polymer has a melting, softening, or glass-transition temperature that is sufficiently low to enable the polymer to flow at the temperature necessary to cure the silicone portion of the coating. Consequently, the hydrophobic polymer ideally has a melting point less than about 210° C. in the case of crystalline hydrophobic polymers or a glass transition temperature less than about 100° C. in the case of amorphous hydrophobic polymers. Examples of non-silicone hydrophobic polymers that can be used include, but are not limited to, polypropylene, polyethylene, waxes, and polycaprolactone. The most preferred non-silicone hydrophobic polymer is a polypropylene wax hydrocarbon mixture such as Micromatte 2000 produced by Micropowders, Inc. The non-silicone hydrophobic polymer can be in the form of a solid, and in particular can be in the form of a micronized powder. The preferred coating is a coating mixture because of the ease in which the coating can be applied. The coating mixture can be prepared by any conventional means for combining the two primary polymer components. For example, the polymers can be combined by mixing, spraying or depositing techniques. Although in many cases the coating may be applied neat, the preferred means for combining the polymers is to mix the polymers with one or more solvents. In a preferred embodiment, the solvent or solvent mixture that is selected will dissolve the silicone polymer. The selected solvent or solvent mixture may or may not dissolve the non-silicone hydrophobic polymer. If the non-silicone hydrophobic polymer does not dissolve in the solvent, then the components form a suspension. The preferred solvents are xylene and Exxon Isopar-k. Ideally, the solvent system will be relatively volatile at ambient conditions.

The most preferred coating mixture of this invention contains approximately by weight, 74.86% Exxon isopar-k, 14.25% xylene, 5.7% hydroxy-terminated polydimethylsiloxane, 5% polypropylene wax hydrocarbon mixture (Micromatte 2000), and 0.19% methylhydrogen siloxane. The approximate acceptable ranges for the ingredients in the preferred mixture are by weight, 1–20% hydroxy-terminated polydimethylsiloxane, 0.5–20% polypropylene wax hydrocarbon mixture, and 0–0.4% methylhydrogen siloxane with the balance of the solution being Exxon isopar-k and xylene in a ratio of approximately, but not limited to, 5.25:1. The preferred approximate ranges are by weight, 2–12% hydroxy-terminated polydimethylsiloxane, 1–9% polypropylene wax hydrocarbon mixture, and 0–0.4% methylhydrogen siloxane with the balance of the solution being Exxon isopar-k and xylene in a ratio of approximately, but not limited to, 5.25:1.

If the silicone polymer selected is in a liquid state, then possibly no solvent addition is necessary to adequately mix the silicone polymer with the non-silicone hydrophobic polymer(s).

The coating mixture can be applied to the contact surface of the medical device using a variety of methods such as dipping, spraying and brushing. The preferred method is to dip the medical device into a solution or suspension of the coating mixture. In this preferred embodiment, the coating must then be exposed to a thermal cycle to volatilize the solvent or solvent mixture and cure the silicone polymer if applicable. The temperature can range from about 140° C. to about 210° C., but it is not limited to this range. The preferred temperature is typically high enough to cause the non-silicone hydrophobic polymers to melt (crystalline or semi-crystalline materials) or soften and flow (amorphous materials), but not high enough to have a detrimental effect on lubricity or durability of the polymer components. For example, exposure to temperatures greater than about 210° C. for extended periods of time cause some silicones to oxidize and form silica, which would decrease lubricity of the coating. The time of exposure to temperature will vary with the polymers being used. In some embodiments, it may be beneficial to melt the non-silicone hydrophobic polymer when the polymer selected is in a solid form. Therefore, the temperature used during the drying/curing cycle may need to be higher than the melting point of the selected non-silicone hydrophobic polymer (for crystalline or semi-crystalline materials), but it is not always necessary that it be completely melted. In the case of amorphous materials, the preferred temperature will be such that it is sufficiently above the glass-transition temperature to cause the non-silicone hydrophobic polymer to flow. For example, in the case of a non-silicone hydrophobic polymer such as polystyrene, which has a critical surface tension of less than 50 mN/m, but a very high glass transition temperature (~100° C.), a processing temperature of 200° C. was insufficient to produce an increase in durability when polystyrene was combined with silicone. This was likely due to the inability to cause polystyrene to flow at 200° C. In addition, the very high stiffness associated with polystyrene likely hinders the ability to significantly improve lubricity. Another example involves the use of polytetrafluoroethylene (PTFE), which has a melting point of approximately 325° C. When PTFE is added to a silicone solution, the lubricity as measured by the first pass penetration force of surgical needles may decrease as a result of improved lubricity, but the durability of the coating may be more difficult to improve.

The use of a temperature sufficient to allow melting or sufficient flow of one or more of the selected polymers in the coating mixture allows those polymers to flow and produces a coating morphology in which the silicone and non-silicone hydrophobic polymers are interspersed, where the silicone polymer typically forms a continuous phase and the non-silicone hydrophobic polymer forms a discontinuous phase. However, this depends on the relative amounts of each polymer. If there is sufficient amount of the non-silicone hydrophobic polymer, then it may form a continuous phase. Regardless whether any of the selected polymers melt, the coating is a multi-phase coating in the most preferred embodiments. A multiphase coating is one that contains two or more phases in the coating after exposure to a thermal cycle to volatilize solvents and/or cure the silicone component of the coating.

In contrast to the application of the coating as a coating mixture to the contact surface of the medical device, the coating can also be applied as a series of layers with a layer of silicone polymer being the outer layer. For example, the non-silicone hydrophobic polymer can be mixed in a suitable solvent and used to provide an inner layer coating on the contact surface of the medical device. The coated surface can then be exposed to an appropriate thermal cycle to volatilize the solvents and melt (for crystalline or semicrystalline materials) the non-silicone hydrophobic polymer or cause it to flow (amorphous materials). The appropriate thermal cycle is dependent on the exact polymers and solvents used in the coating mixture. The contact surface can then be coated with either a mixture of silicone dissolved in solvents or a solventless silicone fluid and processed in a similar fashion to that described previously to form an outer layer of the silicone polymer. If the non-silicone hydrophobic polymer melts, the layers may become interspersed depending on the rheology of the polymers and the thermal cycle used to volatilize solvents and/or cure the silicone component of the coating.

Once the coating is applied to the contact surface of the medical device, and any solvent or solvent mixture used is removed, an amount of the coating effective to provide lubricity to the contact surface without appreciably sacrificing the durability of the coating and consequently its lubricious properties during successive use is applied. As used herein, an effective amount is that amount which will provide the enhanced properties to the contact surface of the medical device as described in the preceding sentence. The approximate preferred amount of the coating on the contact surface of the medical device (without solvents) is about 40- to about 86% by weight of the silicone polymer and about 14- to about 60% of the non-silicone hydrophobic polymer. The most preferred approximate range is about 44 to about 66% by weight of the silicone polymer and about 34 to about 56% of the non-silicone hydrophobic polymer.

Coating performance for medical devices can be tested with a variety of friction and/or adhesion tests. In the case of surgical needles, coating performance and integrity is evaluated using a penetration test device. A coated surgical needle is held using self-locking tweezers or a similar holding device. The coated needle is then passed through a media that is representative of general human tissue. The entire needle is not passed through the media; only approximately half of the needle length is passed through the media and then retracted prior to the next pass. The media is typically a type of polymer or synthetic leather (Porvair or Permair in this example). The needle is then retracted from the media. A typical test includes using 10 needles that are individually passed though the media 10 times each. The maximum force is recorded for each pass and used as a measure of the coating performance. Typically, the penetration force increases with each successive pass as the coating is worn off the needle. Further details of the test equipment and method can be found in U.S. Pat. No. 5,181,416.

EXAMPLES

Example 1

Ethicon BV-1 surgical needles (10.0 mil diameter, no suture attached, see below for a more detailed description) were coated with one of two coating mixtures. The first coating mixture (Mixture #1) contained approximately by weight 6% hydroxy-terminated polydimethylsiloxane, 0.2% methylhydrogen siloxane, 15% xylene, and 78.8% Exxon Isopar-k synthetic isoparrafinic hydrocarbon. This is a conventional one-phase silicone coating (polydimethylsiloxane) after the solvents volatilize that typically provides excellent lubricity, but only moderate durability. This coating mixture is considered a standard baseline and was applied for comparative purposes. The second coating mixture (Mixture #2) contained approximately by weight 5.7% hydroxy-terminated polydimethylsiloxane, 0.19% methylhydrogen siloxane, 14.25%, xylene, 74.86% Exxon Isopar-k synthetic isoparrafinic hydrocarbon, and 5% polypropylene wax hydrocarbon powder mixture with a median particle size of 6–9 microns. This coating mixture is an example of the coating, which is used on the coated medical devices of this invention. BV-1 needles are made from a maraging stainless steel. The needles have a square body geometry and a 12:1 taper point, and are described in detail in U.S. Pat. No. 5,477,604. The needles were coated by hand via a dipping process and placed on a magnetic tray. The tray actually has raised magnetic strips on it in order to hold the proximal ends of the needles secure during the curing cycle and transport while the distal end (tip) of the needles hang over the edge of the magnetic strips. This way, the needle tips do not make contact with the tray. The needles were then heated to 200° C. in a furnace and held for two hours under ambient atmosphere. The needles were then allowed to cool at ambient temperature outside of the furnace. Penetration testing was performed as described above and the results are shown below. The results are from penetration testing done using two sets of 10 needles individually. One set of needles was coated with Mixture #1 and the second set was coated with Mixture #2. The coated needles were penetrated 10 times each. The average penetration force and standard deviation for the two sets of needles for each pass are shown below.

Table 1: Penetration Test Results from needles coated with Mixture #1 and #2 in Example 1

TABLE 1

Penetration Test Results from needles coated with Mixture #1 and #2 in Example 1

| Penetration # | Avg. Force (g) Coating Mixture #1 (Prior Art) | Avg. Force (g) Coating Mixture #2 (Invention) |
|---|---|---|
| 1 | 49 +/− 11 | 41 +/− 4 |
| 2 | 62 +/− 13 | 43 +/− 3 |
| 3 | 76 +/− 11 | 46 +/− 6 |
| 4 | 89 +/− 9 | 47 +/− 7 |
| 5 | 101 +/− 12 | 52 +/− 9 |
| 6 | 111 +/− 12 | 56 +/− 10 |
| 7 | 121 +/− 10 | 61 +/− 10 |
| 8 | 130 +/− 10 | 64 +/− 11 |
| 9 | 135 +/− 12 | 68 +/− 12 |
| 10 | 141 +/− 13 | 74 +/− 11 |

As seen from Table 1 and further illustrated in Graph 1, the needles of this invention coated with Mixture #2, which contain polypropylene wax hydrocarbon mixture, produced a coating that is much more durable and lubricious than the needles of the prior art coated with Mixture #1. The average $10^{th}$ pass penetration force was decreased by 47.5%. Typically, in order to achieve an increase in durability in a medical device coating, the lubricity is sacrificed. However, the addition of polypropylene wax hydrocarbon mixture powder in this specific example to create a two-phase coating gave increased durability without sacrificing lubricity. The same relative results were produced by using identical procedures and coatings on many different needle types manufactured and sold by Ethicon such as: CT-1 (420 stainless steel, 12:1 taper point), PC-1 (maraging stainless steel, cutting edge needles), and CTXB Ethiguard (420 stainless steel, blunt point).

The same procedure as described above was used, but the polypropylene wax hydrocarbon mixture was substituted with polyethylene powder, synthetic wax powder, polypropylene powder, and a modified fluorocarbon polymer powder (containing polyethylene). The result in every case was coated needles with significant improvement in the durability and lubricity relative to that of a needles coated with Mixture #1 as shown in Table 2 below (compare with results of coating Mixture #1 in Table 1).

Table #2: Penetration Test Results of the Needle Coated with Variations of Mixture #2

TABLE #2

Penetration Test Results of Needle Coated with Variations of Mixture #2

| Penetration # | Avg. Force (g) Coating Mixture #2 - Polyethylene substituted for Polypropylene wax hydrocarbon mixture | Avg. Force (g) Coating Mixture #2 - Polypropylene substituted for Polypropylene wax hydrocarbon mixture | Avg. Force (g) Coating Mixture #2 - Synthetic Wax Substituted for Polypropylene wax hydrocarbon mixture | Avg. Force (g) Coating Mixture #2 - Modified Fluorocarbon polymer substituted for Polypropylene wax hydrocarbon mixture |
|---|---|---|---|---|
| 1  | 39 +/- 4  | 49 +/- 5 | 39 +/- 3 | 37 +/- 4 |
| 2  | 47 +/- 4  | 57 +/- 5 | 47 +/- 5 | 43 +/- 5 |
| 3  | 56 +/- 4  | 61 +/- 4 | 57 +/- 5 | 50 +/- 4 |
| 4  | 61 +/- 3  | 65 +/- 3 | 65 +/- 6 | 54 +/- 5 |
| 5  | 66 +/- 5  | 67 +/- 4 | 70 +/- 7 | 63 +/- 6 |
| 6  | 74 +/- 7  | 70 +/- 3 | 75 +/- 9 | 65 +/- 4 |
| 7  | 79 +/- 8  | 69 +/- 5 | 78 +/- 5 | 71 +/- 5 |
| 8  | 83 +/- 10 | 74 +/- 4 | 82 +/- 7 | 76 +/- 4 |
| 9  | 85 +/- 8  | 73 +/- 4 | 84 +/- 6 | 76 +/- 6 |
| 10 | 87 +/- 7  | 76 +/- 4 | 87 +/- 8 | 80 +/- 5 |

Example 2

Ethicon BV-175 surgical needles (7.8 mil, no suture attached, see below for more detailed description) were coated with one of two coating mixtures. The first coating mixture (Mixture #1) contained polydimethylsiloxane, xylene, and Exxon Isopar-k synthetic isoparrafinic hydrocarbon in the same proportions as Coating Mixture #1 in Example 1. This is a conventional one-phase silicone coating (polydimethylsiloxane) after the solvents volatilize that typically provides excellent lubricity, but only moderate durability. This coating mixture is considered a standard baseline and was applied for comparative purposes. The second coating mixture (Mixture #2) was comprised of polydimethylsiloxane, xylene, Exxon Isopar-k synthetic isoparrafinic hydrocarbon, and polypropylene wax hydrocarbon mixture powder with a median particle size of 6–9 microns in the same proportions as Coating Mixture #2 in Example 1. This coating mixture is an example of the coating for the medical devices of this invention. BV-175 needles are made from a maraging stainless steel. These needles have an I-beam body geometry. The needles were coated while on a continuously moving carrier strip in a manufacturing setting as described in U.S. Pat. No. 5,477,604. After coating, the needles were "flash dried" at 225° C. for approximately 30 seconds and taken up on a spool. The needles were then exposed to a temperature of 158° C. for 24 hours and allowed to cool in ambient air. Penetration testing was performed as described in Example 1 above and the results are shown below in Table 3 and Graph 2.

Table 3: Penetration Test Results from needles coated with Mixture #1 and #2 in Example 2

TABLE 3

Penetration Test Results from needle coated with Mixture #1 and #2 in Example 2

| Penetration # | Avg. Force (g) Coating Mixture #1 (Prior Art) | Avg. Force (g) Coating Mixture #2 (Invention) |
|---|---|---|
| 1  | 32 +/- 2 | 27 +/- 2 |
| 2  | 37 +/- 3 | 29 +/- 3 |
| 3  | 43 +/- 4 | 31 +/- 3 |
| 4  | 47 +/- 4 | 32 +/- 4 |
| 5  | 51 +/- 7 | 33 +/- 4 |
| 6  | 54 +/- 6 | 34 +/- 4 |
| 7  | 58 +/- 4 | 35 +/- 5 |
| 8  | 60 +/- 3 | 37 +/- 6 |
| 9  | 61 +/- 5 | 36 +/- 5 |
| 10 | 63 +/- 5 | 39 +/- 7 |

Consistent with the results observed in Example 1, the coated needles of the invention coated with Mixture #2, which contains polypropylene wax hydrocarbon mixture in a two-phase silicone-based coating, exhibited an increase in coating durability without sacrificing lubricity in comparison to prior art needles coated with Mixture #1.

Example 3

Ethicon BV-1 surgical needles (no suture attached, see Example 1 for more detail) were coated with each of the two coating mixtures described in Example 1 (Coating Mixture Nos. 1 and 2), both of which were applied as single layer coatings in the manner described in that example. In addition, a two-layer coating was applied to the needles. The inner coating layer was applied by manually dipping the needles in a mixture of 80 wt % Xylene and 20 wt % polypropylene wax hydrocarbon mixture powder. The needles were then heated to 150° C. and held for 15 minutes under ambient atmosphere. The needles were then allowed to cool to room temperature. These needles were then coated manually to form an outer coating layer with Coating Mixture #1 from Example #1. The needles were then heated to 200° C. and held for two hours under ambient atmosphere. The needles were then allowed to cool at ambient temperature. Penetration testing was performed as described in Example #1 above with the exception that Permair was used as the penetration media. The results are shown below in Table 4 and Graph 3.

Table 4: Penetration Test Results from coatings described in Example #3

TABLE 4

Penetration Test Results from coatings described in Example #3

| Penetration # | Avg. Force (g) Coating Mixture #1 (Prior Art) | Avg. Force (g) Coating Mixture #2 (Invention) | Avg. Force (g) 2-Layer Coating (Invention) |
|---|---|---|---|
| 1 | 11.3 +/− 3 | 11.6 +/− 1 | 10.4 +/− 1 |
| 2 | 11.9 +/− 3 | 11.4 +/− 1 | 10.7 +/− 1 |
| 3 | 12.1 +/− 3 | 11.4 +/− 1 | 10.9 +/− 1 |
| 4 | 12.4 +/− 3 | 11.4 +/− 1 | 11.0 +/− 1 |
| 5 | 13.4 +/− 3 | 11.8 +/− 1 | 11.3 +/− 1 |
| 6 | 14.1 +/− 3 | 11.4 +/− 2 | 11.5 +/− 1 |
| 7 | 14.6 +/− 3 | 12.1 +/− 2 | 11.2 +/− 1 |
| 8 | 15.2 +/− 3 | 11.8 +/− 1 | 11.4 +/− 1 |
| 9 | 16.6 +/− 4 | 12.1 +/− 2 | 11.7 +/− 2 |
| 10 | 17.1 +/− 3 | 12.1 +/− 1 | 11.6 +/− 1 |

As shown in Table 4 and Graph 3, application of the two layer coating onto the needles produces similar penetration performance to that of the single layer coating containing a mixture of the silicone and non-silicone hydrophobic polymer.

Example 4

Ethicon BV-1 surgical needles (no suture attached, see Example 1 for more detail) were coated with one of four coating mixtures. Coating mixture #1 is equivalent to coating mixture #1 described in Example 1. Coating mixture #2 is equivalent to coating mixture #2 described in Example 1. The third coating mixture (Mixture #3) contained approximately by weight 5.7% hydroxy-terminated polydimethylsiloxane, 0.19% methylhydrogen siloxane, 14.25%, xylene, 74.86% Exxon Isopar-k synthetic isoparrafinic hydrocarbon, and 5% Triton-X. The fourth coating mixture (Mixture #4) contained approximately by weight 5.7% hydroxy-terminated polydimethylsiloxane, 0.19% methylhydrogen siloxane, 14.25%, xylene, 74.86% Exxon Isopar-k synthetic isoparrafinic hydrocarbon, and 5% IGEPAL CO-630. Both Triton-X and IGEPAL CO-630 are octylphenoxy polyethoxyethanols that are commonly used as surfactants and dispersing agents in coatings. The needles were coated as described in Example 1. The needles were then heated to 200° C. and held for 2 hours under ambient atmosphere. The needles were then allowed to cool to room temperature. Penetration testing was performed as described in Example #1 and the results are shown below in Table 5 and Graph 4.

Table 5: Penetration Test Results from coatings described in Example 4

TABLE 5

Penetration Test Results from coatings described in Example 4

| Penetration # | Avg. Force (g) Coating Mixture #1 (Prior Art) | Coating Mixture #2 (Invention) | Coating Mixture #3 (Prior Art) | Coating Mixture #4 (Prior Art) |
|---|---|---|---|---|
| 1 | 37 +/− 3 | 40 +/− 2 | 37 +/− 3 | 42 +/− 3 |
| 2 | 50 +/− 5 | 43 +/− 2 | 46 +/− 4 | 58 +/− 5 |
| 3 | 65 +/− 9 | 44 +/− 4 | 54 +/− 3 | 70 +/− 5 |
| 4 | 80 +/− 6 | 48 +/− 4 | 62 +/− 4 | 79 +/− 5 |
| 5 | 93 +/− 8 | 49 +/− 4 | 68 +/− 6 | 88 +/− 7 |

TABLE 5-continued

Penetration Test Results from coatings described in Example 4

| Penetration # | Avg. Force (g) Coating Mixture #1 (Prior Art) | Coating Mixture #2 (Invention) | Coating Mixture #3 (Prior Art) | Coating Mixture #4 (Prior Art) |
|---|---|---|---|---|
| 6 | 101 +/− 10 | 54 +/− 4 | 74 +/− 8 | 91 +/− 8 |
| 7 | 108 +/− 8 | 52 +/− 3 | 79 +/− 9 | 98 +/− 13 |
| 8 | 112 +/− 9 | 57 +/− 4 | 86 +/− 7 | 108 +/− 7 |
| 9 | 113 +/− 13 | 58 +/− 3 | 87 +/− 6 | 110 +/− 8 |
| 10 | 118 +/− 8 | 60 +/− 4 | 91 +/− 8 | 111 +/− 10 |

As shown in Table 5 and Graph 4, the use of coating mixture #3 resulted in a marginal improvement in penetration performance relative to coating mixture #1 and coating mixture #4 resulted in no improvement over coating mixture #1. This example shows that the use of polymeric surfactants and/or dispersing agents such as octylphenoxy polyethoxyethanols combined with silicone do not result in significant increases in durability relative to using silicone only (coating mixture #1), and exhibit appreciably less durability when compared to the penetration performance of the coated needles within the scope of the invention (coating mixture #2).

Example 5

Ethicon PC-1 cutting edge surgical needles (no suture attached) were coated with three coating mixtures. Coating mixtures #1 and #2 are equivalent to coating mixtures #1 and #2 described in Example 1. Coating mixture #3 contained approximately by weight 5.7% hydroxy-terminated polydimethylsiloxane, 0.19% methylhydrogen siloxane, 14.25%, xylene, 74.86% Exxon Isopar-k synthetic isoparrafinic hydrocarbon, and 5% polyethylene glycol. Polyethylene glycol is a well-known hydrophilic polymer (PEG is water-soluble). The needles were coated as described in Example 1 and then heated to 200° C. and held for 2 hours under ambient atmosphere. The needles were then allowed to cool to room temperature. Penetration testing was performed similar to that described in Example #1 (with the exception that only 5 needles per set were tested) and the results are shown below in Table 6.

TABLE 6

| Penetration # | Avg. Force (g) Coating Mixture #1 (Prior Art) | Avg. Force (g) Coating Mixture #2 (Invention) | Avg. Force (g) Coating Mixture #3 |
|---|---|---|---|
| 1 | 40 +/− 2 | 39 +/− 2 | 40 +/− 3 |
| 10 | 84 +/− 7 | 60 +/− 4 | 71 +/− 2 |

Coating Mixture #3 does provide some marginal increase in durability relative to Coating Mixture #1, but exhibits appreciably less durability when compared to the penetration performance of the coated needles within the scope of the invention (coating mixture #2). This example demonstrates the significantly poorer performance of the coated needle when a hydrophilic polymer is substituted for the non-silicone hydrophobic polymer of the coating mixture, which is coated on the needles of this invention.

Example 6

Both ceramic and metallic scalpel blades were coated using coating mixtures #1 and #2 as described in example #1. The lubricity and durability of the coatings were then tested by penetrating the blades into Porvair material using an Instron tensile testing machine and recording the maximum load. The data for the ceramic and metal scalpel blades are shown in Tables 7 and 8 below.

TABLE 7

Ceramic Scalpel Blades

| Penetration # | Force (lbs) Coating Mixture #1 | Coating Mixture #2 |
|---|---|---|
| 1 | 0.67 | 0.63 |
| 2 | 0.71 | 0.65 |
| 3 | 0.73 | 0.66 |
| 4 | 0.77 | 0.68 |
| 5 | 0.78 | 0.68 |
| 6 | 0.81 | 0.69 |
| 7 | 0.83 | 0.69 |
| 8 | 0.86 | 0.70 |
| 9 | 0.88 | 0.70 |
| 10 | 0.87 | 0.76 |

TABLE 8

Metal Scalpel Blades

| Penetration # | Force (lbs) Coating Mixture #1 | Coating Mixture #2 |
|---|---|---|
| 1 | 0.44 | 0.37 |
| 2 | 0.49 | 0.39 |
| 3 | 0.52 | 0.41 |
| 4 | 0.54 | 0.43 |
| 5 | 0.55 | 0.45 |
| 6 | 0.58 | 0.47 |
| 7 | 0.60 | 0.48 |
| 8 | 0.60 | 0.49 |
| 9 | 0.65 | 0.49 |
| 10 | 0.67 | 0.50 |

Coating mixture #2 provided a significant improvement in durability over coating #1 for both the metallic and ceramic scalpel blades Claims

What is claimed is:

1. A medical device having a contact surface exposed repeatedly to bodily tissue, the contact surface being coated with a coating mixture comprising from about 40 to about 86 weight percent of a silicone polymer and from about 14 to about 60 weight percent of a non-silicone hydrophobic polymer.

2. The medical device of claim 1 wherein the silicone polymer is a polyalkylsiloxane.

3. The medical device of claim 2 wherein the polyalkylsiloxane is a polydimethylsiloxane.

4. The medical device of claim 3 wherein the non-silicone hydrophobic polymer has a critical surface tension of less than about 50 mN/m.

5. The medical device of claim 4 wherein the non-silicone hydrophobic polymer is a thermoplastic polymer.

6. The medical device of claim 5 wherein the thermoplastic polymer is flowable at less than about 210 C.

7. The medical device of claim 6 wherein the coating has about 44 to about 66 weight percent of the polydimethylsiloxane and about 34 to about 56 weight percent of the thermoplastic polymer.

8. The medical device of claim 7 wherein the medical device is a surgical needle.

9. The medical device of claim 8 wherein the polydimethylsiloxane is hydroxy terminated.

10. The medical device of claim 9 wherein the thermoplastic polymer is polyethylene, polypropylene or polycaprolactone.

11. The medical device of claim 1 wherein the coating comprises a mixture of an hydroxy terminated polydimethylsiloxane and a non-silicone hydrophobic polymer selected from the group consisting of polyethylene, polypropylene and polycaprolactone.

12. The medical device of claim 11 wherein the coating mixture has about 44 to about 66 weight percent of the hydroxy terminated polydimethylsiloxane and about 34 to about 56 weight percent of the non-silicone hydrophobic polymer.

13. The medical device of claim 12 wherein the medical device is a surgical needle.

* * * * *